United States Patent [19]

Johnson et al.

[11] 4,013,680
[45] Mar. 22, 1977

[54] PROCESS FOR THE PREPARATION OF AROMATIC α-KETO CARBOXYLIC ACIDS

[75] Inventors: Martin Godfrey Johnson, Rickmansworth; John Peter Turnbull, London; Harold Alfred Crisp, Harrow Weald, all of England

[73] Assignee: Glaxo Laboratories Limited, Greenford, England

[22] Filed: June 18, 1975

[21] Appl. No.: 587,813

[52] U.S. Cl. .................. 260/332.2 A; 260/347.3; 260/523 A
[51] Int. Cl.$^2$ ...................................... C07D 333/24
[58] Field of Search ............... 260/332.2 A, 523 A, 260/347.3

[56] References Cited
OTHER PUBLICATIONS

Hartough "Thiophene and its Derivatives" (1952) p. 382.
Harrison "Compendium of Organic Synthetic Methods" (1971) p. 57.

Primary Examiner—James O. Thomas, Jr.
Assistant Examiner—A. Siegel
Attorney, Agent, or Firm—Bacon & Thomas

[57] ABSTRACT

A process is described for the preparation of aryl α-keto acids in which the corresponding methyl ketone or aldehyde is oxidized in aqueous solution with an inorganic nitrite salt and hydrochloric or sulfuric acid.

7 Claims, No Drawings

PROCESS FOR THE PREPARATION OF AROMATIC α-KETO CARBOXYLIC ACIDS

This invention relates to the preparation of carboxylic acids and in particular to the preparation of α-keto acids (i.e. substituted glyoxylic acids) by the oxidation of the corresponding methyl ketones.

α-Keto acids have many uses and a variety of methods are available for their preparation. Arylglyoxylic acids and their derivatives, particularly in the furan and thiophene series, are valuable intermediates in the preparation of penicillins and cephalosporins. These compounds are of course desirably prepared from the most readily available starting materials and in a number of cases, particularly in the case of the aromatic glyoxylic acids just referred to, the starting material of choice is the corresponding methyl ketone (i.e. the corresponding acetyl derivative). In the furan and thiophene series for example such acetyl derivatives can readily be prepared by acylation, for example with acetic anhydride.

A number of methods have been suggested in the past for oxidising these methyl ketones to the desired α-keto acids. For example, the use of selenium dioxide as the oxidising agent in this step is known, but although this can give satisfactory results the reagent is toxic and needs to be handled with great care. The use of potassium permanganate has also been suggested, for example in the oxidation of acetyl thiophenes, but the manganese dioxide produced in the reaction creates waste disposal problems. Moreover, the oxidation of acetylfuran with potassium permanganate is very unsatisfactory, giving only poor yields of the required compound.

We have now found that the oxidation may be conducted with a mixture of an inorganic nitrite salt and an acid. The use of these reagents presents much less of a waste disposal problem and tests we have carried out have shown that the yield of the desired product can be much greater. For example, the oxidation of 2-acetylfuran to fur-2-ylglyoxylic acid with sodium nitrite under acid conditions can give yields of the acid double those obtained by use of potassium permanganate. The use of inorganic nitrite salts as oxidising agents has been suggested in the past in only very rare instances and their use in the oxidation of methyl ketones to glyoxylic acids has never previously been described.

Thus the invention provides a process for the preparation of α-keto acids of the formula R.CO.COOH in which R is a carbocyclic or heterocyclic aryl group, which comprises oxidising the corresponding methyl ketone of the formula $R.CO.CH_3$ in aqueous solution with an inorganic nitrite salt and hydrochloric or sulphuric acid.

The reaction is conveniently carried out in aqueous solution using as the nitrite salt an alkali metal or alkaline earth metal salt (preferably a sodium salt). The acid is preferably hydrochloric acid.

In the starting materials of the formula $R.CO.CH_3$, examples of the R groups are monocyclic and fused ring aryl groups, e.g. benzofuryl and phenyl, and unsaturated carbonattached heterocyclic groups having 5-7 ring members and containing one or more hetero atoms (e.g. O, N or S, particularly O or S). These groups may either be unsubstituted or substituted, for example by one or more $C_{1-6}$ alkyl or alkoxy, aryloxy or nitro groups, The starting material must of course be stable to the acidic conditions used in the reaction, and the R group should not itself be oxidised under the reaction conditions. R is preferably a heterocyclic aryl group.

The reaction may for example be used in the preparation of phenyl-, furyl-, and thienylglyoxylic acids (i.e. compounds of the formula R.CO.COOH where R is a fur-2- or 3-yl, thien-2- or 3-yl or phenyl group), and is particularly suitable when R is a furyl group.

The reaction is preferably carried out at elevated temperatures of for example 40°–100° C, preferably 60°–95° C. The optimum temperature will of course depend on several factors and particularly on the nature of the starting material.

The reaction may be performed in a number of different ways but we have found in our tests that the yield of the desired acid can be increased by carrying out the reaction in two stages between which the pH is raised and in each of which the nitrite salt is added steadily throughout the reaction period. Thus for example in the first stage of the reaction the nitrite salt may be steadily added (e.g. 2–3 moles nitrite per mole ketone, as an aqueous solution) to an aqueous solution of the starting material and a mineral acid over a period of ½–4 hours, preferably 1–2 hours, at the desired temperature. The pH is then raised to about 1.5 to 2.5, e.g. about 2, e.g. with a buffering agent such as trisodium phosphate, (which may be formed in situ from phosphoric acid and sodium hydroxide), sodium borate or disodium phthalate, or with a nitrite salt. More nitrite salt (e.g. 1.5–2.5 moles per mole of ketone) may then be added to the reaction mixture in a second stage for example over a period of ½–4 hours, preferably 1–2 hours. The reaction will usually be completed in the second stage (as shown by thin layer chromatography), but if necessary more nitrite salt may be added. The keto acid produced may then be recovered from the reaction mixture either as the free acid or a salt by conventional extraction techniques, although in some cases it may be used in further reactions without isolation.

We believe that the oxidation reaction of the invention proceeds via the formation of an aldehyde intermediate, R.CO.CHO. In the two stage reaction technique just described, we thus believe that in the first stage the methyl ketone is oxidised to the aldehyde, which is then oxidised to the acid in the second stage. It will be appreciated that where the aldehydes of formula R.CO.CHO are available from other sources, the oxidation method of the invention may be applied to them directly to give the desired α-keto acids.

As indicated above, the process of the invention may be used as one stage in the preparation of penicillins and cephalosporins and particularly cephalosporins having at the 7-position a side chain containing a furyl or thienyl group. Thus for example thiophene or furan may first be acylated to give 2-acetylthiophene or 2-acetylfuran, which may then be oxidised by the process of the invention to thien-2-yl- or fur-2-yl glyoxylic acid; the latter acids may if desired be suitably modified (e.g. by conversion into their oximes) and converted into the corresponding acid chlorides for reaction with a 7-amino cephalosporin.

The following examples illustrate the invention. Temperatures are in °C. "T.l.c." refers to thin layer chromatography.

EXAMPLE 1

Concentrated hydrochloric acid (B. P., 196 ml), was added to a stirred mixture of 2-acetylfuran (44 g) in water (600 ml) at 65° C and then a solution of sodium nitrite (168 g) in water (800 ml) added steadily below the surface over 1¾ hours. A further amount of sodium nitrite (28 g) in water (150 ml) was added over 20 minutes raising the pH to 3.4. After 1 hour at 65° more sodium nitrite (12 g) in water (60 ml) was added raising the pH to 4.4. After 40 minutes the solution was cooled to room temperature, filtered and sodium chloride (320 g) added and the solution extracted with methylene chloride (3 × 200 ml). Evaporation of the methylene chloride left a residue of 2-acetylfuran (11.0 g; 25%). The aqueous layer was adjusted to pH 2.8 (hydrochloric acid) and extracted with ethyl acetate (4 × 200 ml). Evaporation of the extracts gave furoic acid (3.8 g; 9%). The aqueous layer was adjusted to pH 0.2 with hydrochloric acid and extracted with ethyl acetate (5 × 200 ml), the organic extracts being washed sequentially with saturated sodium chloride solution. The organic phase was evaporated to an oil which was taken up in ethyl acetate (150 ml) treated with charcoal and evaporated to give an orange-yellow solid. This was crystallised from methylene chloride, and second and third crops obtained by evaporation. Total yield of fur-2-ylglyoxylic acid: 27.4 g (49%), m.p. 95°–98°.

EXAMPLE 2

To a stirred solution of 2-acetylfuran (22.0 g, in water (85 ml) and concentrated hydrochloric acid (B.P., 105 ml) at 65° was added steadily a solution of sodium nitrite (35.0 g) in water (100 ml) over 90 minutes. Warm 1.3 M trisodium phosphate (180 ml) was then added over 3 minutes to raise the pH of the solution to 1.9. Simultaneously, steady addition of a second solution of sodium nitrite (28 g) in water (70 ml) was commenced, which took 90 minutes to complete. The solution was stirred for a further 45 minutes at its final pH of 4.1, then acidified with hydrochloric acid to pH 2.5 and treated with 20% aqueous urea (10 ml) for 10 minutes to destroy any excess of nitrite. The pH of the solution was then raised to 3.5 by addition of aqueous sodium hydroxide and the mixture was cooled to room temperature.

Extraction of the mixture with methylene chloride (2 × 100 ml) and evaporated of the extracts in vacuo afforded unreacted 2-acetylfuran (2.6 g; 12%). UV assay of the aqueous solution at this stage indicated a 72% yield of fur-2-ylglyoxylic acid. The pH of the mixture was lowered to 3.0 by addition of hydrochloric acid, sodium chloride (100 g) was added and the mixture was extracted with ethyl acetate (4 × 100 ml), readjusting the pH to 3.0 between extractions. Evaporation of the combined extracts in vacuo gave a brown solid (1.8 g; 8%) the main component of which was furoic acid.

Concentrated hydrochloric acid (80 ml) was added to the aqueous solution to lower the pH to 0.2. Extraction with ethyl acetate (5 × 100 ml), followed by washing of the combined extracts with saturated aqueous sodium chloride (2 × 150 ml), and evaporation in vacuo gave an oil (24.4 g). Dilution of the stirred oil with methylene chloride (25 ml) followed 15 minutes later by light petroleum (b.p. 40°–60°, 50 ml), afforded crystalline fur-2-ylglyoxylic acid (16.8 g; 60%) m.p. 95°–98°; λ max 285 nm ($E_{1\ cm}^{1\%}$ 1015).

EXAMPLE 3

To a solution of 2-acetylfuran (22 g) in water (100 ml) and concentrated hydrochloric acid (B.P., 100 ml) at 65°, sodium nitrite (42 g) in water (100 ml) was added over 90 minutes. A solution of trisodium orthophosphate dodecahydrate (50.5 g) in warm water (200 ml) was added over 15 minutes with vigorous stirring, when the pH rose to 1.8. This was followed by addition of a solution of sodium nitrite (28 g) in water (70 ml) over 90 minutes. After 1 hour the solution was worked up as in Example 1. Extraction with methylene chloride (2 × 100 ml) at pH 4.7 gave unreacted 2-acetylfuran (1.35 g; 6.1%). Extraction with ethyl acetate (4 × 100 ml) at pH 3.0 yielded furoic acid (2.6 g; 12.1%). The combined organic phases after extraction with ethyl acetate (5 × 100 ml) at pH 0.1 were washed with sodium chloride solution and then stirred with water (150 ml) and solid sodium bicarbonate added to bring the pH to 4. An ultraviolet spectroscopic assay of the sodium salt solution taking the $E_{1\ cm}^{1\%}$ of pure acid at λ max 285 nm as 1020 indicated a yield of 17.0 g (60.8%).

EXAMPLE 4

2-Acetylfuran (22 g) was treated as in Example 2 except that the 1.3M sodium phosphate solution was replaced by a 1.7M solution of sodium borate (180 ml), to raise the pH to 1.8.

After continuing as in Example 2 and extracting with methylene chloride at pH 3.5 to remove 13% 2-acetylfuran, a UV assay of the aqueous layer indicated a yield of fur-2-ylglyoxylic acid of 17.7 g (63%).

EXAMPLE 5

To a solution of 2-acetylfuran (22 g) in water (110 ml) and concentrated hydrochloric acid (95 ml) at 65°, a solution of sodium nitrite (42 g) in water (90 ml) was added over 90 minutes. This was followed by trisodium phosphate solution (prepared from 11.75 ml phosphoric acid and 150 ml 4N sodium hydroxide) to bring the pH to 2, and then sodium nitrite (28 g) in water (90 ml) was added over 90 minutes. Towards the end of the addition hydrochloric acid was added to keep the pH at 3.5. After half an hour the solution was cooled at 20° and extracted with methylene chloride (100, 75, 50 ml) to remove 2-acetylfuran (1.8 g; 8.2%). The pH was adjusted to 3 with hydrochloric acid and the solution extracted three times with ethyl acetate (100, 75, 50 ml) to remove furoic acid (1.8 g). The aqueous layer was adjusted to pH 0.2 with hydrochloric acid, salt added (100 g) and extracted with ethyl acetate (100, 90, 80, 70, 60 ml). The combined extracts were washed with saturated sodium chloride solution and evaporated under reduced pressure to 30 ml. Methyl alcohol (100 ml) was added and the solution filtered and the filtrate stirred at room temperature while a solution of sodium ethyl hexanoate (25% in methanol) was added to pH 3.85 (121 ml required). The sodium salt of fur-2-ylglyoxylic acid was filtered off, washed with methanol and dried at 40° in vacuo (17.05 g; 52.6%). A second crop was obtained by evaporation of the mother liquors (1.6 g; 4.9%). The $E_{1\ cm}^{1\%}$ of the first crop at λ max 284.5 nm was 840.

The potassium salt of fur-2-ylglyoxylic acid was prepared by the same basic technique, modified as follows after the ethyl acetate extraction: the combined ethyl acetate extracts were evaporated to low volume and diluted with methanol (200 ml). A solution (37 ml) of 4 N potassium hydroxide in methanol was added with stirring. The precipitated potassium salt of fur-2-ylglyoxylic acid was filtered off, washed with IMS and dried at 40° in vacuo (17.0 g; 47.6%), $\lambda_{max}$ 284 nm, $E_1 {}_{cm}^{1\%}$ 780. A second crop (3.6 g; 10.1%) was obtained by evaporation of the filtrate.

EXAMPLE 6

2-Acetylfuran (22 g) in 6N hydrochloric acid (200 ml) at 65° was treated with a solution of sodium nitrite (35 g) in water (100 ml) over 95 minutes. A 1.3M solution of disodium phthalate (230 ml) was added over 5 minutes whilst a solution of sodium nitrite (28 g) in water (70 ml) was being added over 85 minutes. One hour after the end of the addition of the nitrite the solution was cooled and acidified of pH 1.4 with hydrochloric acid and the precipitated phthalic acid filtered off. The solution was next adjusted to pH 3.5 and extracted with methylene chloride (2 × 100 ml) to remove unreacted 2-acetylfuran (1.8 g; 8%), then adjusted to pH 2.8 and extracted with ethyl acetate (4 × 100 ml) to remove furoic acid and phthalic acid (8.6 g) and finally adjusted to pH 0.2 and extracted with ethyl acetate (5 × 100 ml). Evaporation of the ethyl acetate gave 18 g (64.3%) of fur-2-ylglyoxylic acid m.p. 81°–91° C.

EXAMPLE 7

A mixture of water (2 liters), concentrated hydrochloric acid (1.75 l) and 90% $H_3PO_4$ (0.18 l) and acetylthiophene (0.52 kg) was stirred and heated to 90°–95°. With continued stirring and heating at 90°–95°, a solution of sodium nitrite (0.828 kg) in water (2 liters) was added over 1½ hours. More sodium nitrite (0.552 kg) in water (1.4 liters) + 48%w/w NaOH (0.5 liters) was added at 90°–95° with stirring over 1½ hours; the pH of the reaction mixture rose to 3.7 and a little tar separated. After cooling to 25° the clear solution was decanted from the tar and adjusted to pH 3 with concentrated hydrochloric acid. Extraction with isopropyl ether (2 l, 1.5 l,) 2 × 1 l) was carried out to remove thienoic acid before more concentrated hydrochloric acid was added, bringing the pH to less than 1. The acidified aqueous layer was extracted with ethyl acetate (2 l, 3 × 1 l) and the ethyl acetate extracts, which contained thienylglyoxylic acid, were combined and treated with 0.88 SG ammonia until pH 9 was reached. Ammonium thienylglyoxylate crystallised from the ethyl acetate solution, was filtered off, washed with ethyl acetate and dried in air at 40° to give the product as a brownish solid (0.52 kg, 72.7%th.) T.l.c. showed this to be substantially ammonium 2-thienylglyoxylate containing ca. 0.25% of thienic acid.

EXAMPLE 8

A solution of sodium nitrite (35g; 0.5 mole) in water (100 ml.) was added steadily over 95 minutes to a stirred mixture of 2-acetylthiophene (25.1g; 0.2 mole) in 6N-hydrochloric acid (200ml) at 65°. 1.3M Trisodium phosphate (160 ml). was then added over ca 3 minutes to raise the pH of the mixture to 1.8. Simultaneously, addition of a second portion of sodium nitrite (28g; 0.4 mole) in water (70 ml.) was commenced which took 75 minutes to complete. The pH was kept below 3.5 by addition of hydrochloric acid as required, during the nitrite addition, and was then lowered to 2. Urea (2g.) in water (10 ml.) was then added to decompose any excess of nitrite. The mixture was cooled to 20° and extracted first at pH 5.7 with methylene chloride (2 × 100 ml.) to give crude unreacted 2-acetylthiophene (3.6g; 14%), then at pH 2.7 with methylene chloride (3 × 100 ml.) to give crude thienoic acid (1.4g; 6%), and finally at pH 0.2 with methylene chloride (5 × 100 ml) followed by ethyl acetate (3 × 100 ml). These latter extracts were washed with saturated sodium chloride, and evaporated to dryness. Crystallisation of the residue from methylene chloride — light petroleum (b.p. 40°–60°) gave thien-2-ylglyoxylic acid as two crops of bright yellow prisms [19.8g (63.5%), m.p. 92°–94°, and 3.0g (9.6%) m.p. 91°–93°].

EXAMPLE 9

A solution of sodium nitrite (35g; 0.5 mole) in water (100 ml.) was added steadily over 95 minutes to a stirred mixture of acetophenone (24.0g; 0.2 mole) in 6N-hydrochloric acid (200 ml.) at 65°. 1.3M Trisodium phosphate (165 ml.) was then added over ca. 3 minutes to raise the pH of the mixture to 1.8. Simultaneously, addition of a second solution of sodium nitrite (28g; 0.4 mole) in water (70 ml.) was commenced, which took 75 minutes to complete. The pH of the mixture was kept below pH 3.5 during the nitrite addition by addition of hydrochloric acid as required, then was lowered to pH 2. Urea (2g) in water (10 ml.) was then added to decompose any excess of nitrite. The mixture was cooled to 20°, and extracted at pH 4.2 with chloroform (2 × 100 ml.) to give a mixture of unreacted acetophenone and benzoic acid (3.8 g; 16%). The aqueous layer was further acidified with 10N hydrochloric acid (50 ml.) and extracted with ethyl acetate (5 × 100 ml.). The combined water-washed extracts were evaporated to dryness and the residual oil (30g.) was crystallised from carbon tetrachloride (25 ml.) to give phenylglyoxylic acid as almost colourless prisms (9.2g; 31%) m.p. 63.5°–65.5°. Dilution of the mother liquors with increasing quantities of light petroleum (b.p. 40°–60°) gave further crops of phenylglyoxylic acid [8.7g (29%) m.p. 60°–64°, and 1.6g (5%)].

EXAMPLE 10

To a stirred solution of 2-acetylfuran (22.0 g.) in 8N-aqueous sulphuric acid (300 ml.) at 65°, a solution of sodium nitrite (34.5 g) in water (80 ml.) was added during 90 minutes. Sodium phosphate solution (prepared from 31 ml. of phosphoric acid and 400 ml. of 4N-sodium hydroxide) containing sodium nitrite (4.4 g.) was then added during 23 minutes to give a pale green reaction solution with pH 1.58. Further sodium nitrite (65.5 g.) in water (170 ml.) and 4N-sodium hydroxide (50 ml.) were added simultaneously during 3 hours. After 20 minutes, the solution was cooled to 25° and extracted with methylene chloride (100, 75 ml.) to remove 2-acetylfuran (3.8 g.; 17%). The pH was adjusted to 3 with hydrochloric acid (7 ml.) and extracted with ethyl acetate (2 × 100 ml.) to remove furoic acid (2.25 g.). The aqueous phase was acidified with hydrochloric acid (200 ml.), and extracted with ethyl acetate (5 × 100 ml.). The combined extracts were washed with saturated sodium chloride solution (25 ml.) and the organic layer was evaporated under reduced pressure to a low volume (ca. 20 ml.). The residue diluted with methanol (100 ml.), cooled to 10° and stirred while 4N-potassium hydroxide in methanol (21.5 ml.) was added slowly to give a suspension with pH 5. The mixture was stored at 5° overnight and then the potassium fur-2-ylglyoxylate (11.45 g.; 31.1%, not allowing for the recovery of 2-acetylfuran) was collected by filtration, washed with IMS (60 ml.) and dried in vacuo. A second crop (2.75 g.; 7.7%) was obtained from the concentrated mother liquors. The $E_{1\ cm}^{1\%}$ of the first crop at $\lambda_{max}$ 285 nm was 760.

EXAMPLE 11

2-Acetylfuran (22.0 g.) in 4N-hydrochloric acid (0.3 l.) was stirred at 66°–67° while potassium nitrite (42.55g.) in water (90 ml.) was added during 90 minutes. Potassium phosphate solution (prepared from 14.9 ml. of phosphoric acid and 193 ml. of 4N-potassium hydroxide) containing potassium nitrite (2.8 g.) was added during 10 minutes to give a reaction mixture with pH 1.9. A further solution of potassium nitrite (53.15 g. in 120 ml. of water) was added during 120 minutes with the reaction held at pH 3 to 3.5 by adding hydrochloric acid as required. After half-an-hour, the reaction mixture was cooled to 20° and extracted twice with methylene chloride (2 × 70 ml.) to remove unreacted 2-acetylfuran (1.3 g.; 6%). Hydrochloric acid (5 ml.) was added to the aqueous layer which was extracted with ethyl acetate (2 × 75 ml.) to remove furoic acid (1.4 g.). Sodium chloride (140 g.) and hydrochloric acid (70 ml.) were added to the aqueous phase and the product extracted into ethyl acetate and isolated as in the Example 10. Two crops of potassium fur-2-ylglyoxylate (20.0 g.; 56% and 3.45 g.; 9.7%) were obtained. The $E_{1\ cm}^{1\%}$ of the first crop at $\lambda_{max}$ 285 was 767. The second crop has $E_{1\ cm}^{1\%}$ 710.

We claim:

1. A process for the preparation of an α-keto acid of the formula R.CO.COOH in which R is selected from the group consisting of phenyl, thienyl, furyl and benzofuryl, which process comprises oxidizing in a first stage the corresponding methyl ketone of the formula R.CO.CH$_3$ in aqueous solution with an inorganic nitrite salt and hydrochloric or sulphuric acid, raising the pH to about 1.5 to 2.5 and completing the oxidation in a second stage by adding more of said nitrite salt to the reaction mixture, said process being carried out at a temperature of 40°–100° C with from 2–3 moles nitrite salt per mole ketone being added in said first stage and from 1.5–2.5 moles nitrite salt per mole of ketone being added in said second stage.

2. A process as claimed in claim 1 wherein R is a phenyl, thienyl or furyl group.

3. A process as claimed in claim 1 wherein the nitrite is an alkali metal or alkaline earth metal nitrite.

4. A process as claimed in claim 3 wherein the nitrite is sodium or potassium nitrite.

5. A process as claimed in claim 1 wherein the reaction temperature is 60° to 95° C.

6. A process as claimed in claim 1 wherein the nitrite salt is added steadily.

7. A process as claimed in claim 1 wherein the acid is hydrochloric acid.

* * * * *